United States Patent [19]
Neidleman et al.

[11] Patent Number: 4,567,144
[45] Date of Patent: Jan. 28, 1986

[54] METHOD OF PRODUCING LONG CHAIN WAX ESTERS FROM ETHANOL

[75] Inventors: Saul L. Neidleman, Oakland; Jacqueline L. Ervin, Pinole, both of Calif.

[73] Assignee: Cetus Corporation, Emeryville, Calif.

[21] Appl. No.: 408,254

[22] Filed: Aug. 16, 1982

[51] Int. Cl.$^4$ .......................... C12P 7/64; C12R 1/265
[52] U.S. Cl. .................................... 435/134; 435/240; 435/247; 435/859
[58] Field of Search ..................... 426/7; 435/134, 135, 435/136, 247, 253, 822, 859, 142

[56] References Cited

U.S. PATENT DOCUMENTS 3,409,506 11/1968 Stevens et al.
4,152,278 5/1979 Bell.
4,404,283 9/1983 Neidleman et al. ................. 435/134

OTHER PUBLICATIONS

Stewart et al., *J. Bacteriol.*, 78:726-730 (1959), Bacterial Hydrocarbon Oxidation.
Raymond et al., *Adv. Appl. Microbiol.*, 14:93-121 (1971), Biochemical Activities of Nocardia.
Krasilnikov et al., *Mikrobiologiya*, 38:757-760 (1969), Formation of Cetyl Palmitate from N-Hexadecane by a Culture of Mycobacterium STRAIN 3'.
Stewart et al., *Science*, 132:1254 (1960), Esters from Bacterial Oxidation of Olefins.
Finnerty et al., *Journal of Bacteriology*, 250-258 (1975), Comparative Analysis of the Lipids of Acinetobacter Species Grown on Hexadecane.
Gallagher et al., *Journal of General Microbiology*, (1971), 68, 245-247, Occurrence of Waxes in Acinetobacter.
Fixter et al., *Biochemical Society Transactions* 504-505 (1976), The Effect of Growth Conditions on the Wax Content of Various Strains of Acinetobacter.
Guehler, et al., *Archives of Biochemistry and Biophysics* 106, 294-298 (1964), Microbiological Transformations XIII, Composition of the Wax Formed by Euglena Gracilis.
Du Preez, et al., Applied Microbiology and Biotechnology (1981) 13:45-53, Growth Parameters of Acinetobacter Calcoaceticus on Acetate and Ethanol.

*Primary Examiner*—Raymond Jones
*Assistant Examiner*—Marianne M. Cintins
*Attorney, Agent, or Firm*—Albert P. Halluin; Elliott L. Fineman; Thomas E. Ciotti

[57] ABSTRACT

A process for producing wax esters having the general structural formula $RCO_2R'$, where R and R' are radicals selected from the group consisting of $CH_3(CH_2)_a CH = CH(CH_2)_b$- and $CH_3(CH_2)_c$- where $a+b = 12-14$ for R and 13-15 for R' and where $c = 14-16$ for R and 15-17 for R'. The method includes aerobically incubating a culture of microorganisms of the genus Acinetobacter species HO1-N, in an aqueous mineral salts solution containing ethanol as a primary food source. Incubation is performed at a temperature known to produce a desired percentage of diene, monoene and saturated R and R' moieties in the mixture.

6 Claims, No Drawings

METHOD OF PRODUCING LONG CHAIN WAX ESTERS FROM ETHANOL

BACKGROUND AND SUMMARY

The present invention relates to a process for making long chain wax esters biosynthetically. More particularly, the invention relates to the biosynthesis of wax esters by incubating a microorganism of the species Acinetobacter aerobically in the presence of ethanol as a primary food source.

Long chain wax esters are required in a variety of specialized industrial applications. One important application is in steel making, where a recently developed continuous casting process depends on continuous and reliable lubrication of the mold walls. U.S. Pat. No. 4,152,278 discloses lubricant compositions, comprising wax esters of fatty acids and alcohols, which are particularly advantageous in the continuous casting of steel. These wax esters contain either 0, 1, 2, 3 or 4 internally located carbon-carbon double bonds, with no more than 2 double bonds in either of the fatty acid or the fatty alcohol segments. Presently, these wax esters are derived from vegetable oil derivatives by a relatively complicated chemical synthesis involving reduction of long chain fatty acids to fatty alcohols, followed by esterification with fatty acids. Compositions prepared in this way are limited by the carbon chain length and by the degree of unsaturation in the original vegetable oil derivatives.

Also in the field of lubrication, there exists a need for synthetic, extreme pressure and antiwear lubricant additives. Such additives prevent destructive metal-to-metal contact in lubrication under high pressure and/or temperature conditions, such as occur in certain gear elements in automotive vehicles and in various industrial machines. General chemical properties which make wax esters useful as lubricant additives are carbon chain lengths of at least 14 carbons in both the fatty acid and fatty alcohol segments, and the presence of an internal carbon-carbon double bond in one or both of the segments.

In the past, the only known natural source of such lubricant-additive waxes has been the sperm whale, an endangered species. More recently, waxes derived from the jojoba plant have been used as lubricants and additives. The esters derived from jojoba oil are composed almost entirely of straight chain acids and alcohols, each segment being predominantly 20-22 carbon atoms in length and having one unsaturated bond. In laboratory testing, jojoba oil has been found comparable or superior to sperm oil as a lubricant additive. The disadvantage of this wax ester source is plant growth time—up to five years—between the time of planting and first harvesting of the waxes.

Microorganisms are a potential source of wax esters. Through metabolic action, wax esters can be produced from inexpensive, readily available hydrocarbons. For example, U.S. Pat. No. 3,409,506 describes the production of wax esters by *Micrococcus cerificans* (now referred to as Acinetobacter species HO1-N) from aliphatic hydrocarbon feed stocks. A characteristic of wax esters produced in this microbial system is that the principal wax esters will have a carbon chain length in the fatty acid and fatty alcohol segments equal to the chain length of the hydrocarbon used as a feed stock. This feature permits the fatty acid and fatty alcohol chain lengths in the wax ester to be controlled by the chain length of the feed stock used.

A major disadvantage of microbial production of wax esters from aliphatic hydrocarbon chain feed stocks, as reported in the prior art, is that saturated, rather than unsaturated, wax esters are formed. Above-cited U.S. Pat. No. 3,409,506 discloses that *Micrococcus cerificans* produces only cetyl palmitate saturated wax ester from hexadecane. Stewart et al., *J. Bact.* 78:726-730 (1959) state that *Micrococcus cerificans* produces only octadecyl stearate saturated wax ester from octadecane. Makula et al., *J. Bact.* 121:250-258 (1975) claim that only cetyl palmitate saturated wax ester is formed by Acinetobacter sp. HO1-N acting on hexadecane. Raymond et al., *Adv. Appl. Microbiol.* 14:93-121 (1971) and Krasilnikov et al., *Mikrobiologiya* 38:757-760 (1969) state the same finding (hexadecane going to cetyl palmitate wax ester only) for Nocardia species and Mycobacterium species, respectively.

Attempts have been made to produce wax esters containing carbon-carbon double bonds by feed stocks other than saturated hydrocarbons. The metabolic action of *Acinetobacter* sp. HO1-N (Makula et al., *J. Bact.* 121:250-258 (1975)) and 3 species of Acinetobacter (Gallagher, *J. Gen. Microbiol.* 68:245-247 (1971)) on amino acid feed stocks yielded unsaturated wax esters. Fixter et al., *Biochem. Soc. Transl.* 4:504-505 (1976), reported that the metabolic action of Acinetobacter species on acetate or succinate feed stocks yielded wax esters containing $C_{14}$, $C_{16}$ and $C_{18}$ saturated and monounsaturated fatty acid and fatty alcohol segments. The metabolic action of *Candida lipolytica* on olefinic feed stocks yielded unsaturated wax esters (Stewart et al., *Science* 132:1254 (1960)). Both types of feed stocks yielding unsaturated wax esters are substantially more expensive than aliphatic hydrocarbons.

Guehler et al., *Arch. Biochem. Biophys.* 106:291-298 (1964) have reported the formation of wax esters by *Euglena gracilis* grown on a complex nutrient medium containing acetate and ethanol. The esters formed were saponified and the acids and alcohols and acids were converted into methyl esters and acetates, respectively. Analysis of these components by vapor phase chromotography showed a predominance of saturated $C_{12}$, $C_{13}$ and $C_{14}$ linear chains in both the methyl ester and acetate fractions. Only small quantities of monounsaturated chains, including hexadecenoic acid (0.7%), heptadecenoic acid (0.1%) and octadecenoic acid (0.1%) were present.

One object of the present invention is to provide a method of producing, by microbial biosynthesis, wax esters having above-mentioned characteristics suitable for use as lubricants and lubricant additives.

Another object of the invention is to provide such a method which employs, as a microbial food source, inexpensive and readily available biomass-based feed stocks.

Yet another object of the invention is to provide such a method in which the degree of unsaturation of fatty acid and alcohol segments in the wax esters can be varied selectively by changing the temperature conditions employed in the method.

The invention includes a process for producing a mixture of wax esters having the general formula $RCO_2R'$, where R and R' are each radicals selected from the group consisting of $CH_3(CH_2)_a CH=CH(CH_2)_b-$, where $a+b$ equals 12-14 for R and 13-15 for R', and $CH_3(CH_2)_c-$, where c equals 14-16 for R and 15-17 for R'. The process includes aerobically incubating a culture of microorganisms of the genus Acinetobacter in an aqueous mineral salts solution containing ethanol as a primary food source, and extracting the wax esters produced by the microorganisms.

In a preferred embodiment of the invention, the process includes selecting an incubation temperature known to produce, in such a wax esters mixture, a desired percentage of diene, monoene and saturated wax esters.

These and other objects and features of the invention will become more clearly understood by referring to the following description and claims.

DETAILED DESCRIPTION OF THE INVENTION

Microorganisms for use in the present invention include bacteria of the genus Acinetobacter capable of producing long chain wax esters during incubation on a food source consisting primarily of ethanol. The preferred microorganism is Acinetobacter species HO1-N, also known as *Micrococcus cerificans*. The ATCC registration number of Acinetobacter species HO1-N is 14987.

Ethanol used as a food source in the method of the invention may be obtained advantageously by fermentation of one of the large variety of readily available and inexpensive biomass-based feedstocks, such as unprocessed cane juice, grain starch, hydrolyzed cellulose, and the like. The ethanol may also be obtained by acid hydrolysis of wood or enzymatic hydrolysis of cellulose.

Wax ester mixtures are produced in accordance with the invention by aerobically cultivating microorganisms in an aqueous mineral salts solution to which ethanol feed has been added. Standard incubation techniques well known to those skilled in the art can be used. One preferred incubation method and reactor for Acinetobacter species HO1-N are detailed in above-mentioned U.S. Pat. No. 3,409,506, which is incorporated herein by reference.

Oxygen is supplied to the incubation vessel conveniently as an oxygen-containing gas, e.g., air, containing between about 19 and 22 mole percent oxygen.

Nitrogen is supplied to the incubation mixture from any organic or inorganic nitrogen-containing compound capable of releasing nitrogen in a form utilizable by the microorganism. For reasons of economy, it is usually desirable to use an inorganic nitrogen-containing compound such as ammonia, ammonium hydroxide or ammonium salts such as ammonium chloride. Selected minerals such as potassium, sodium, zinc, magnesium, manganese and copper necessary for microorganism growth are also added to the growth medium, preferably in the form of soluble inorganic salts, to form what is referred to herein as a mineral salts solution. The pH of the salts solution is adjusted initially to between about 7.0 and 7.5, and preferably about 7.2 by a suitable buffer system, e.g., a phosphate buffer system.

The degree of carbon-carbon double bond unsaturation in the wax ester mixture produced by the method of the invention varies with the temperature at which the incubation is performed. The production of wax esters at incubation temperatures ranging from 17° C. to 30° C. will be discussed herein. A greater temperature range compatible with growth of the microorganism is contemplated.

Bacterial cultures used in the present invention grown may be maintained conveniently on a conventional agar-based medium. Cells are grown up in an aqueous culture by incubation under optimal growth conditions, and the cells are pelleted by centrifugation, washed in buffer and repelleted by centrifugation. Washed, resuspended cells are transferred to a mineral salts solution to produce an initial cell concentration of preferably between about $1-3 \times 10^6$ cells, per ml in a suitable incubation vessel.

After the addition of ethanol to a preferred final concentration of between about 0.2%-1% (v/v), the medium is incubated with continuous stirring or agitation. The incubation period is determined typically by the time required to reach a steady state level of wax esters at a particular incubation temperature. The steady-state incubation period may range from between about 24 hours at an incubation temperature of 30° C. to 54 hours at 17° C.

The wax esters mixture produced is extracted from the incubation medium using conventional extraction solvent systems, such as acetone or chloroform/methanol. The extract may be dried down by heating or evaporation.

The process of the present invention will be illustrated more particularly by the following examples.

EXAMPLE I

Acinetobacter species HO1-N, ATCC Number 14987, was grown and maintained on an agar-based medium composed of Meuller Hinton broth (21 grams/liter) and agar (20 grams/liter). The organism was grown for 1 day at 25° C. The cells were used immediately to innoculate seed cultures, or were stored for up to 30 days at 4° C. prior to use.

A seed stage of the microorganism was initiated by transferring the culture from the agar culture into aqueous Mueller Hinton broth (21 grams/liter). Incubation was carried out under shaking conditions (200 rpm), at 30° C. for 16 hours. After incubation the cells were pelleted at 6,000 rpm for 10 minutes and washed in 0.1 M $KPO_4$ buffer, pH 7.0, and recentrifuged as before. The washed, pelleted cells were resuspended in an original volume of 0.1 M $KPO_4$ buffer, pH 7.0.

Cell incubation was performed in a mineral salt solution having the following composition:

| Component | Concentration ml/liter |
|---|---|
| 1.0 M $KH_2PO_4$ | 22 |
| 0.5 M $Na_2HPO_4$ | 56 |
| 1.0 M $NH_4Cl$ | 25 |
| 0.5 M $K_2SO_4$ | 1 |
| 1.0 mM $ZnSO_4.7H_2O$ | 3 |
| 0.5 M $MgSO_4.7H_2O$ | 0.5 |
| 1 mM $MnSO_4.4H_2O$ | 3 |
| 1.0 mM $CuSO_4.5H_2O$ | 0.2 |

The pH of the solution was adjusted to about 7.2, and 50 ml of the medium was introduced into a 125 ml glass Erlenmeyer flask and sterilized at 121° C. for 15 minutes.

After the salts solution had cooled, ethanol was added aseptically to the flask to a final volume of 0.5% (v/v). One ml of the washed, resuspended cells was introduced into the flask. The flask was placed in a two inch stir shaker and the cells incubated at 24° C. for 30 hours at a shaking speed of about 200 rpm.

The contents of the flask were extracted with two 50 ml volumes of chloroform/methanol (2:1) by shaking in a separatory funnel. After the liquid in the funnel had settled, the bottom organic layer (an emulsion) was drawn off and centrifuged at 5,000 rpm for 10 minutes at 20° C. Three clear layers were noted: a lower, organic layer, a middle cell layer and an upper aqueous layer. The lower organic layer was carefully removed by syringe and the solvent evaporated by heating the extract on a heating block at about 75°, using boiling chips. Depending on the incubation temperature, typically about 15–30 mg wax esters per liter of incubation medium were recovered.

The composition of wax esters in the extract was analyzed by capillary gas chromatography (hereafter GC). A 30 meter SE-54 fused-silica capillary column, operated at 200° C.–325° C. at 10° C. per minute temperature programming, was attached to a Finnigan 4021 gas chromatography mass spectrometer (hereafter GCMS). Wax ester samples were dissolved in a suitable volume of chloroform, and 3 microliters of the dissolved sample were injected onto the column in a split mode (split ratio of 30:1). A flame ionization detector was used to detect wax ester peaks in the chromatogram. Mass spectrometer structure identification of the chromatogram peaks was performed by operating the mass spectrometer at 70eV electron impact ionization.

GC analysis using flame ionization detection yielded 9 predominant wax ester peaks on the chromatogram, these being labeled as peaks 1–9 in Table I below. The table shows the retention time, expressed in minutes, for each peak in the gas chromatography separation. These particular retention times correspond to those of known available wax esters which are identified in the third column in the table.

TABLE I

| GC Peak | Retention Time (minutes) | Known Wax Ester |
|---|---|---|
| 1 | 12.2 | hexadecenyl hexadecenoate |
| 2 | 12.5 | hexadecenyl hexadecanoate |
| 3 | 12.8 | hexadecanyl hexadecanoate |
| 4 | 13.6 | |
| 5 | 13.9 | hexadecenyl octadecenoate |
| 6 | 14.3 | hexadecanyl octadecanoate |
| 7 | 14.9 | |
| 8 | 15.2 | octadecenyl octadecanoate |
| 9 | 15.5 | octadecanyl octadecanoate |

Each of the 9 wax ester peaks was further characterized by mass spectographic analysis. Peak 1 had a molecular weight of 476 and 2 diagnostic fragment mass ions of mass 222 and 236. This mass spectrum was identical to that of an authentic sample of hexadecenyl hexadecenoate. Peak 2 had a molecular weight of 478 and 4 diagnostic fragment mass ions of mass 222, 224, 236 and 257. This mass spectrum was identical to that of a mix of an authentic sample of hexadecenyl hexadecanoate and hexadecanyl hexadecenoate. Peak 3 had a molecular weight of 480 and 2 diagnostic fragment mass ions of mass 224 and 257. This mass spectrum was identical to that of an authentic sample of hexadecanyl hexadecanoate. Peak 4 had a molecular weight of 504 and 4 diagnostic mass ions of mass 222, 236, 250 and 264. This mass spectrum was identical to that expected from a mix of hexadecenyl octadecenoate and octadecenyl hexadecenoate. Peak 5 had a molecular weight 506 and 8 diagnostic fragment mass ions of mass 222, 224, 236, 250, 252, 257, 264 and 285. This mass spectrum was identical to that of a mix of authentic samples of hexadecenyl octadecanoate, hexadecanyl octadecenoate, octadecanyl hexadecenoate and octadecenyl hexadecanoate. Peak 6 had a molecular weight of 508 and 4 diagnostic fragment mass ions of mass 224, 252, 257 and 285. This mass spectrum was identical to that of a mix of authentic samples of hexadecanyl octadecanoate and octadecanyl hexadecanoate. Peak 7 had a molecular weight of 532 and 2 diagnostic fragment mass ions of mass 250 and 264. This mass spectrum was identical to that expected from octadecenyl octadecenoate. Peak 8 had a molecular weight of 534 and 4 diagnostic fragment mass ions of mass 250, 252, 264 and 285. This mass spectrum was identical to that of a mix of authentic samples of octadecenyl octadecanoate and octadecanyl octadecenoate. Peak 9 had a molecular weight of 536 and 2 diagnostic fragment mass ions of mass 252 and 285. This mass spectrum was identical to that of an authentic sample of octadecanyl octadecanoate.

The data just discussed are summarized in Table II. The data are arranged in four groups, corresponding the four general structural formulae shown.

TABLE II

| Group 1 $CH_3(CH_2)_a CH=CH(CH_2)_b CO_2(CH_2)_c CH=CH(CH_2)_d CH_3$ | | |
|---|---|---|
| GC peak | a + b | c + d |
| 1 | 12 | 13 |
| 4 | 12,14 | 15,13 |
| 7 | 14 | 15 |

| Group 2 $CH_3(CH_2)_a CH=CH(CH_2)_b CO_2(CH_2)_c CH_3$ | | |
|---|---|---|
| GC peak | a + b | c |
| 2 | 12 | 15 |
| 5 | 12,14 | 17,15 |
| 8 | 14 | 17 |

| Group 3 $CH_3(CH_2)_a CO_2(CH_2)_c CH=CH(CH_2)_d CH_3$ | | |
|---|---|---|
| GC peak | a | c + d |
| 2 | 14 | 13 |
| 5 | 14,16 | 15,13 |
| 8 | 16 | 15 |

| Group 4 $CH_3(CH_2)_a CO_2(CH_2)_c CH_3$ | | |
|---|---|---|
| GC peak | a | c |
| 3 | 14 | 15 |
| 6 | 14,16 | 17,15 |
| 9 | 16 | 17 |

EXAMPLE II

In this example, separate incubations of Acinetobacter species HO1-N grown on an ethanol food source at 17° C., 24° C. and 30° C. were performed. The incubation periods used were those found to produce a steady state or near steady state level of wax esters in the incubate at the associated temperature. These incubation times were 24 hours at 30° C., 30 hours at 24° C., and 52 hours at 17° C. All other incubation conditions were identical to those described in Example I.

The wax esters produced by incubating Acinetobacter species HO1-N in an ethanol food source at each of the three different incubation temperatures were extracted and analyzed by gas chromatography in the manner described in Example I. Thus, for each of the three different-temperature incubates, the wax-ester extract was analyzed by gas chromatography to produce a multi-peak chromatogram having up to 9 peaks corresponding to those characterized in Example I. The amount of ester associated with each peak was quantitated by a conventional peak integration method. The data, which are summarized in Table III, are expressed in terms of diene, monoene and saturated chain fractions. The diene fraction in Table III includes esters associated with Group 1 in Table II, the monoene fraction includes esters associated with Groups 2 and 3, and the saturated fraction includes esters associated with Group 4.

TABLE III

| Reaction Temperature | Di-Ene Fraction | Mono-Ene Fraction | Saturated Fraction |
|---|---|---|---|
| 17° C. | 72% | 18% | 10% |
| 24° C. | 29% | 40% | 31% |
| 30° C. | 9% | 25% | 66% |

As can be seen from Table III, incubation of Acinetobacter species HO1-N at 17° C. results in the microbial production of primarily diene long chain wax esters, whereas incubation of the cells at 30° C. results in the production of predominantly saturated long chain wax esters. Incubation cells at 24° C. results in a "balanced" mixture of diene, monoene unsaturated long chain wax esters.

From the foregoing description and examples, it can be seen how various objects of the present invention are achieved. The invention provides a method of producing, by microbial biosynthesis, long chain wax esters having an internal unsaturated bond in one or both of the acid and alcohol segments. The wax esters are thus well suited for use as lubricants and lubricant additives in high temperature and/or high pressure appliations and should provide a suitable replacement for wax esters of this type which heretofore have been available only from sperm whale or jojoba plant sources, or through relatively expensive chemical synthetic techniques.

A further advantage of the invention is that the food source for the microbial transformation includes, as a major component, ethanol which may be derived readily and inexpensively from fermentation of a variety of different types of biofeed mass. The process of the invention can thus be incorporated in a biofeed mass fermentation operation in which some or all of the ethanol generated in the operation is used in the microbial production of valuable wax esters.

It has also been shown herein that the process of the invention can be adapted, by cell incubation at a selected temperature, to produce a mixture of wax esters having a desired distribution of diene, monoene and saturated esters. In particular, the method of the invention can be adapted by incubation at a relatively low temperature, to produce a mixture of wax esters which are particularly enriched in those monoene and diene type esters which are known to be most valuable as lubricant and lubricant additives.

While preferred examples of the present invention have been described herein, it will be apparent to those skilled in the art the various changes and modifications can be made without departing from the spirit of the invention.

What is claimed is:

1. A process for producing a mixture of wax esters having the general formula $RCO_2R'$, where R and R' are each radicals selected from the group consisting of:
   I. $CH_3(CH_2)_aCH=CH(CH_2)_b—$, where $a+b=12-14$ for R and 13-15 for R', and
   II. $CH_3(CH_2)_c—$, where $c=14-16$ for R and 15-17 for R', said process comprising
   aerobically incubating a culture of microorganisms of the genus Acinetobacter in an aqueous mineral salts solution containing ethanol as a primary food source, and
   extracting the wax esters mixture produced by said incubating.

2. The process of claim 1, wherein the microorganism includes Acinetobacter species HO1-N, ATCC No. 14987.

3. The process of claim 1, which further includes performing the incubation at one of a first and a second temperature to produce a mixture of wax esters having a major portion of saturated R and R' moieties, and a major portion of monounsaturated R and R' moieties, respectively.

4. The process of claim 3, wherein the first and second temperatures are about 30° C. and 17° C., respectively.

5. A process for producing a mixture of wax esters including, predominantly, esters having the following general formulas:
   I. $CH_3(CH_2)_aCH=CH(CH_2)_bCO_2(CH_2)_cCH=CH(CH_2)_dCH_3$
   II. $CH_3(CH_2)_aCH=CH(CH_2)_bCO_2(CH_2)_{c+d+2}CH_3$
   III. $CH_3(CH_2)_{a+b+2}CO_2(CH_2)_cCH=CH(CH_2)_dCH_3$
   IV. $CH_3(CH_2)_{a+b+2}CO_2(CH_2)_{c+d+2}CH_3$ where $a+b=12-14$ and $c+d=13-15$, said process comprising
   selecting an incubation temperature known to produce in such a mixture a desired percentage of diene, monoene and saturated wax esters of the above formulas,
   aerobically incubating, at such a selected temperature, a culture of Acinetobacter species HO1-N, ATCC No. 14987, in an aqueous mineral salts solution containing ethanol as a primary food source, and
   extracting the wax esters mixture produced by said incubation at such temperature.

6. The process of claim 5, wherein the incubation temperatures are selected from within a temperature range of between about 17° C. and 30° C., at which temperatures the mixtures contain a major portion of wax esters of the general formulas I and IV, respectively.

* * * * *